Figure 1:
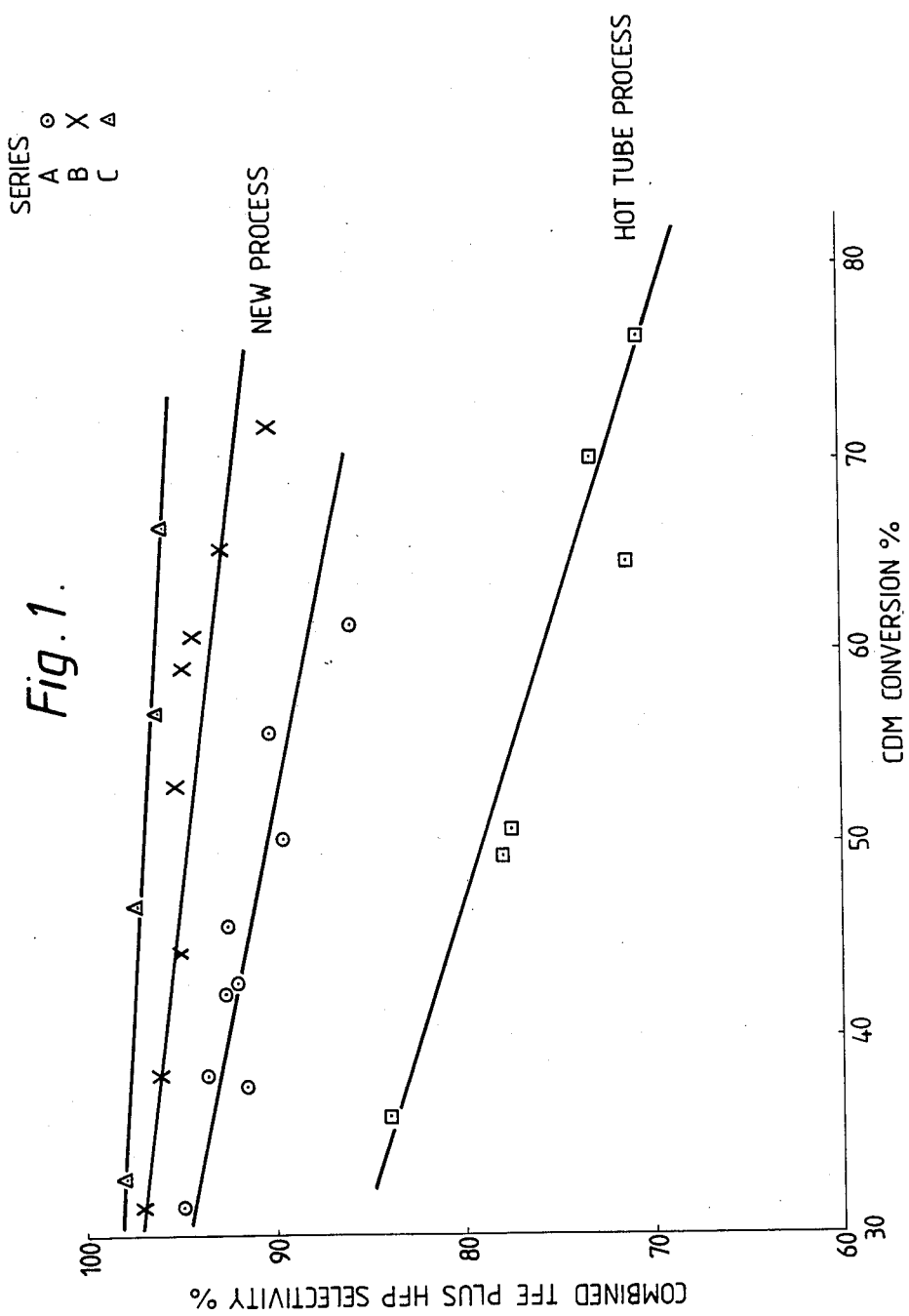

United States Patent [19]

Cresswell et al.

[11] Patent Number: 4,849,554
[45] Date of Patent: Jul. 18, 1989

[54] PRODUCTION OF TETRAFLUOROETHYLENE AND HEXAFLUOROPROPYLENE

[75] Inventors: David L. Cresswell, Christleton; Eric W. Sims, Widnes, both of England

[73] Assignee: Imperial Chemical Industries plc, London, England

[21] Appl. No.: 171,649

[22] Filed: Mar. 22, 1988

[30] Foreign Application Priority Data

Apr. 10, 1987 [GB] United Kingdom ............... 8708618

[51] Int. Cl.$^4$ .................. C07C 17/24; C07C 17/26; C07C 21/18
[52] U.S. Cl. .................. 570/159; 422/200; 422/239
[58] Field of Search ........................ 570/159

[56] References Cited

U.S. PATENT DOCUMENTS

| 2,994,723 | 8/1961 | Scherer et al. | 570/159 |
| 3,308,174 | 3/1967 | Edwards et al. | 570/159 |
| 3,338,980 | 8/1967 | Gozzo | 570/159 |

FOREIGN PATENT DOCUMENTS

| 723699 | 12/1965 | Canada | 570/159 |
| 1061377 | 3/1967 | United Kingdom | 570/159 |

Primary Examiner—J. E. Evans
Attorney, Agent, or Firm—Cushman, Darby & Cushman

[57] ABSTRACT

Production of tetrafluoroethylene and hexafluoropropylene in very high combined selectivity by pyrolysis of chlorodifluoromethane, optionally using gaseous diluent wherein the pyrolysis is effected under substantially isothermal and uniform conditions, the reaction temperature is within the range 750°–980° C. (preferably 800°–980° C.), and the gaseous residence time is within the range 1 to 50 milliseconds. A fluidphase electromagnetic induction reactor suitable for effecting the process is described.

12 Claims, 3 Drawing Sheets

PRODUCTION OF TETRAFLUOROETHYLENE AND HEXAFLUOROPROPYLENE

The present invention relates to a process for the production of tetrafluoroethylene (TFE) and hexafluoropropylene (HFP).

It is known to manufacture TFE by the pyrolysis of chlorodifluoromethane (CDM) according to the overall reaction:

$$2CHClF_2 \rightleftharpoons C_2F_4 + 2HCl$$

The reaction is a gaseous phase one and can be effected at above 600° C. by passing CDM on its own through a heated tube. The reaction is endothermic from left to right but is not detected analytically (after reasonable contact times) below about 400° C. The CDM only partially reacts and the conversion of CDM to products at equilibrium increases with increasing temperature and reduce pressure. The reaction suffers from the disadvantage of a lack of selectively towards TFE formation and by-products are formed by competing reactions, leading to compounds such as hexafluoropropylene, perfluoroisobutylene, chlorohexafluoropropane, and chlorotetrafluoroethane among many others. The selectively can be maximised by carefully controlling the reaction conditions, notably temperature, pressure and residence time (in the reactor tube) although any increase in selectivity is always offset by a decrease in conversion.

It is known to improve this selectivity/conversion compromise by conducting the pyrolysis in the presence of a diluent (which is substantially inert under the reaction conditions being used), particularly steam, whereby CDP and superheated steam are passed in admixture through a hot tube at a reaction temperature of typically about 650°-850° C. and a residence time of typically about 30 to 500 milliseconds so as to undergo a substantially adiabatic reaction (see GB Pat. Nos. 1041738, 960309 and 904022). Using this technique it is possible according to GB No. 904022 to achieve selectivities in the range 90-94% at conversions of 65-70% by employing steam/CDM mixtures containing 15-70 mole % steam (i.e. 85-30 mole % CDF); according to GB Pat. No. 1047138 it is possible to achieve selectivities in the range 90-95% at conversions of 75-85% by employing steam/CDM mixtures containing 70-90 mole % steam (i.e. 30-10 mole % CDF); GB Pat. No. 960309 exemplifies very high selectivities in the range 95-98% at conversions of 50-96% (the results are rather variable) by employing steam/CDM mixtures containing 83-96 mole % steam (i.e. 17-4 mole % CDM). To the best of our knowledge all commercial production of TFE from the pyrolysis of CDM is performed either at lowish CDM conversion by passing pure CDM through a hot metal tube or at higher CDM conversions by using the technique of passing a steam/CDM mixture through a hot metal tube, and it is evident that in order to achieve very high selectivities at reasonably high conversions in the latter case the mixture must comprise a very high proportion of steam (and in actual practice we have found the prior art teaching to be really too optimistic and found that steam levels of about 80 mole % only allow the attainment of selectivities of about 75-95%, with conversions of about 35-78% being achieved). This need to raise very large volumes of steam has its own disadvantages however, e.g. the cost involved in the generation and handling of such large quantities of steam and the risk of further by-products such as CO being formed by steam-reforming reactions.

It is also known from U.S. Pat. No. 3,306,940 to produce hexafluoropropylene (HFP) by the pyrolysis of CDM, whereby a mixture of HFP, TFE, perfluorocyclobutane (PCB) and other products are formed. While the proportion of HFP formed is low at low CDM conversion, it is found that the proportion of HFP increases markedly in the range 86 to 94% CDM conversion. Such a reaction in U.S. Pat. No. 3,306,940 is said to be performed at a temperature in the range of 700° to 900° C., under a pressure preferably of 0.5 to 1.2 atmospheres and over a time period of 0.1 to 10 seconds; the reaction is also performed in a hot tube reactor. Presumably the formation of HFP occurs by the addition of $CF_2$:, produced e.g. from CDM decomposition and perhaps from TFE decomposition, to initially formed TFE:

$$C_2F_4 + :CF_2 \rightarrow C_3F_6$$

Although a comparatively high proportion of HFP is formed at 86 to 94% CDM conversion in the hot tube, the reaction is by no means a clean one, and other products (besides TFE) such as PCB, are still formed in significant proportion. Moreover the CDM conversion range for effective HFP production is narrow; above about 90% CDM conversion the yield of unwanted products itself shows a sharp increase and beyond about 94% CDM conversion production becomes impractical due to carbon deposits choking the reactor.

Similarly, in prior art processes where the CDM pyrolysis is geared for the production of TFE, the reaction is not clean, and several by-products additional to HFP are formed in relatively high proportion, even when the conditions are optimised (by steam dilution) to yield high selectively of TFE production.

It is further known from U.S. Pat. No. 3,459,818 to produce TFE plus HFP from the pyrolysis of CDF in a combined selectivity of 75 to 80% by employing a hot tube reactor down which a defined temperature gradient is maintained and where the CDF also contains a certain proportion of TFE. However, the reaction is still not as clean as it might be since other by products are formed in quite high yield over a large range of conversion (e.g. $C_4F_8$) as indicated in the patent). Moreover, the essential requirement for TFE as a component of the pyrolysis feed material is a limiting feature.

We have now discovered a process for the production of a mixture of TFE and HFP from the pyrolysis of CDM (alone or optionally in admixture with other materials) which provides an exceptionally high selectivity for the combined production of TFE and HFP irrespective of the conversion of CDM and irrespective of the individual selectivity of TFE and HFP formation in the reaction.

According to the present invention there is provided a process for the production of tetrafluoroethylene (TFE) and hexafluoropropylene (HFP) which process comprises passing a gaseous flow of chlorodifluoromethane (CDM), optionally in admixture with a gaseous or vaporous diluent, through a hot reaction zone wherein it is subjected to a pyrolysis reaction to form tetrafluoroethylene and hexafluoropropylene, followed by quench cooling of the exit flow of gas from the reaction zone, and wherein said process is subject to the following combination of conditions:

(1) the pyrolysis in the reaction zone is effected under isothermal conditions which are applied substantially uniformly to all parts of the gas passing through the zone;

(2) the temperature in the reaction zone is controllable and within the range of from 750° to 980° C.; and (3) the gaseous residence time in the reaction zone is within the range of from 1 to 50 milliseconds (more preferably from 1 to 25 milliseconds).

In this specification by conversion is meant the mole fraction (expressed as a percentage) of the CDM that undergoes reaction in the pyrolysis. By selectivity of TFE and/or HFP production is meant:

$$\frac{2 \times \text{no. of moles of TFE and/or } 3 \times \text{no. of moles of HFP produced}}{2 \times \text{no. of moles of TFE} + 3 \times \text{no. of moles of HFP} + \text{no. of other products produced normalized to a C1 (i.e. unitary carbon) basis}} \times 100\%$$

(i.e. for combined selectivity, read "and" in the and/or alternative).

Using the process of the invention it is possible to achieve very high selectivity of TFE plus HFP combined irrespective of CDM conversion, irrespective of the individual selectivities of the TFE and HFP formation in the reaction and irrespective of whether CDM is pyrolysed neat or in admixture with another fluid material(s).

For example, FIG. 1 of the accompanying drawings show the combined selectivity to TFE plus HFP as a function of CDM conversion for the pyrolysis of 100 mole % CDM in the new process (curve for series A) in comparison with the performance of a hot metal tube (current practice). In the claimed process, the selectivity of TFE formation decreases from ≧90% at about 10 to 20% CDM conversion to 60% at about 60% CDM conversion, while the selectivity of HFP formation will increase from <5% selectivity at about 10 to 20% CDM conversion to about 25% selectivity at about 60% CDM conversion. However, the combined selectivity to TFE plus HFP under such conditions is ≧85% irrespective of CDM conversion (with less than 15% of other products being formed); indeed for a wide range of conversion the combined selectivity is well over 90%. In comparison, the combined selectivity of TFE plus HFP in the hot metal tube is always less than in the new process by at least 10% irrespective of the CDM conversion.

Figure 2:
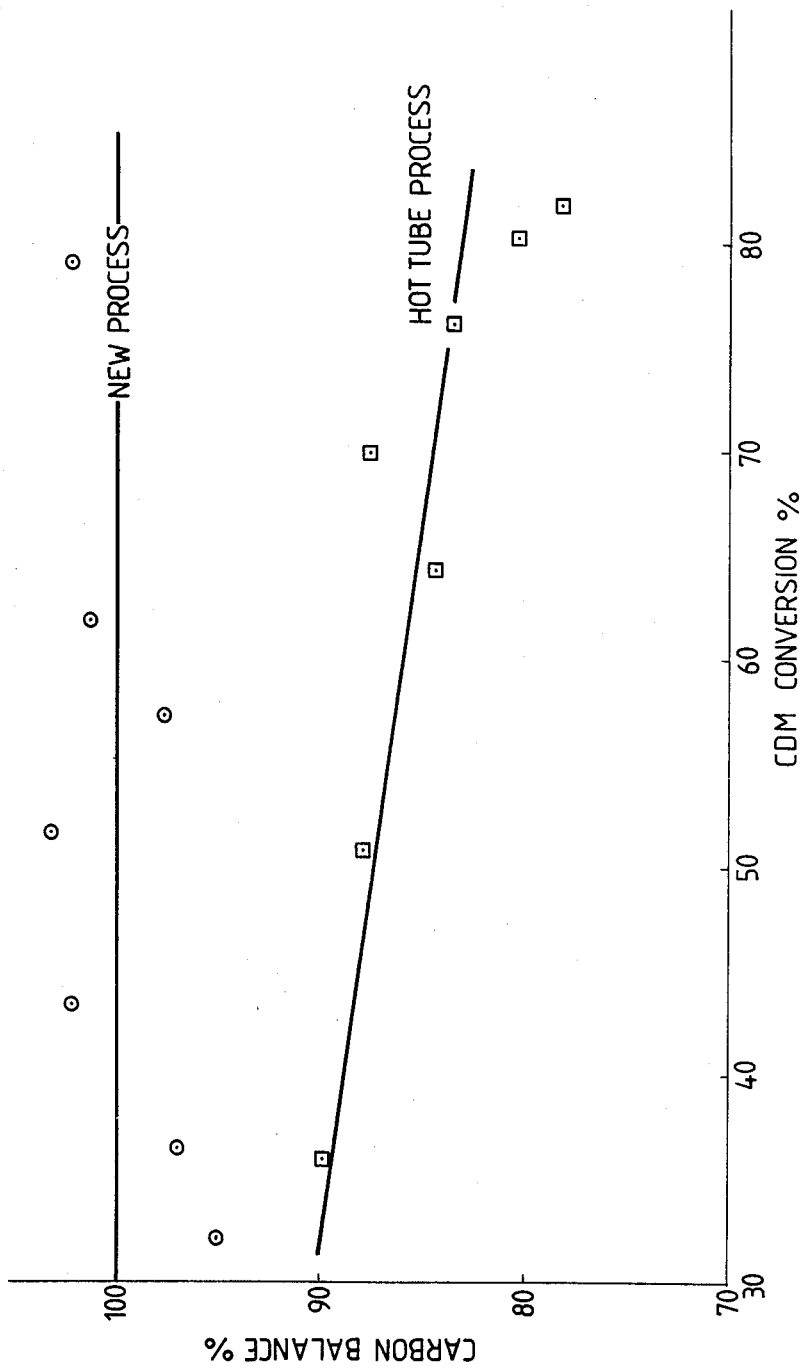

In actual practice, the performance of the process according to the invention is even better than these results indicate, for while essentially quantitative carbon balances are obtained with the new process, as much as 20% of the CDM fed to the hot tube reactor ends up as carbon - see FIG. 2 of the accompanying drawings.

Accordingly it is seen that the process of the invention can be readily employed for the production of TFE and HFP from the same plant, it being only necessary for the reactor conditions to be suitably varied or tailored to achieve desired relative proportions of either TFE or HFP. For example, the conditions may be varied to maximise the proportion of TFE in the product mix or the proportion of HFP, or indeed any intermediate TFE/HFP product ratio between such values may be readily obtained. The products TFE and HFP and starting material CDM may be separated by conventional methods, this being relatively more easily effected than in prior processes in view of the very small proportion of any other product(s) being produced. In particular, very little dimer (cyclic $C_4F_8$) is formed (such dimer formation having been a problem in prior processes for TFE/HFP production in that expensive equipment was required for its removal even though it possesses little intrinsic value in itself as an end product). Chlorotrifluoroethylene (CTFE) is the other main by-product; this material azeotropes with HFP and means to separate it therefrom may be employed if required.

Where the process of the invention is being used primarily as a process for HFP production, it is found that the overall yield of HFP may be further increased by recycling a part of the exit fluid to the CDM feed gas, after having removed HCl (e.g. using NaOH) and water (e.g. using a condenser), this exit fluid containing the mixture of TFE and HFP products. This can double or even triple the HFP yield obtainable using a single pass. On an industrial scale, an even better overall yield could be obtainable by removing substantially all impurities in the exit fluid and all the HFP so that only TFE (and possibly the cyclic dimer $C_4F_8$ which can further pyrolyse to HFP) is recycled to the CDM feed gas.

The isothermal uniformly applied conditions of the process of the invention, the reaction temperature within the elevated range of from 750° to 980° C. (typically 800° to 980° C.), and the short residence time employed, enables a very intensive production process to be provided of exceptionally good productivity.

Where the process of the invention is being employed primarily as a process for TFE production, the reaction temperature utilized is preferably within the range 750° to 890° C. (the range 800°–880° C. being typical) as this will assist in the maximisation of the proportion of TFE in the product mix. Where the process of the invention is being used as a source of HFP as well as TFE production the reaction temperature utilized is preferably within the range 840° to 980° C. (the range 900° to 950° C. being typical) as this will assist in the maximisation of the proportion of HFP in the product mix.

The quench cooling time of the exit gas to a lower temperature (usually just below the temperature at which the desired reaction proceeds), starting from the time the exit gas leaves the reaction zone, should preferably be within a period of about 50 milliseconds, although quench time can be difficult to estimate accurately. The quench time does have a small effect on selectivity, but not very much (perhaps of the order of about 2%).

The defined residence time is intended to include the time taken in the reaction zone for the entry gas to warm up from a low entry temperature (usually about or near ambient or a temperature intermediate between 750° C. and about or near ambient) to the desired temperature in the reaction zone.

The residence time employed in the process of the invention should be within the range of from 1 to 50 milliseconds, preferably 1 to 25 milliseconds; this will allow the production of both HFP and TFE in selectivities suitable for individual recovery if appropriate reaction zone temperatures are used. In cases where the process of the invention is being employed primarily as a source of TFE production, the residence time is more preferably within the range of from 1 to 10 milliseconds, particularly 1 to 4 milliseconds as this will further assist in the maximisation of the proportion of TFE in the product mix.

Conventional or obvious conveyance means may be used to convey the flow of gas to and from the reaction zone; these normally comprise one or more suitably connected ducts of suitable configuration. The exit flow of reacted gas mixture which includes TFE, HFP, unreacted CDM, and (if used) diluent, may be handled by conventional techniques (e.g. condensation, freezing, distillation etc) in order to isolate and collect the TFE, HFP, unreacted CDM, diluent gas (if used), or any other constituent (or to effect a recycling process as described above).

In the process of the invention, if a diluent gas is used it should be substantially inert under the reaction conditions being used; examples of possible diluent gases include nitrogen and carbon dioxide. Steam is not inert under the reaction conditions employed in the process of the invention and may react to yield unwanted impurities such as CO and HF; accordingly its use is not recommended. The use of a diluent gas will certainly increase yet further the combined selectivity to TFE and HFP in the process of the invention at any value of CDM conversion (see examples and FIG. 1). However such use will entail the cost of removing the diluent from the product and is therefore not usually preferred in the process of the invention. From this point of view (i.e. ease of separation) carbon dioxide does represent a preferred possibility for use as a diluent in commercial-scale operation of the process of the invention, since it could be more readily removed than other inert gases.

It is apparent that the prior art technique of passing CDF through a hot tube (optionally with superheated steam) cannot be used to effect the reaction conditions required for the process of the present invention because such a reactor will provide adiabatic (and not isothermal) reaction conditions. It would also be very difficult (though not impossible) from a practical viewpoint (i.e. when operating on a plant scale) to achieve a gaseous residence time of not more than 50 milliseconds (and particularly not more than 10 milliseconds) in the reaction zone using the prior art tube reactor, particularly when operating at higher temperatures (say above 900° C.) and when requiring a precise control of temperature distribution. Furthermore, the use of the hot tube reactor incurs well below quantitative carbon mass balances as mentioned supra. In view of all this, a different type of reactor is required.

It is found that the process of the present invention may be carried out very effectively using a fluid-phase electromagnetic induction heated reactor which, e.g., comprises:

(a) an inductively-heatable fluid-permeable reactor element which is inductively heatable to a controllable temperature(s) of at least within the range of 750° to 980° C. to provide an isothermal reaction zone therein when fluid to be reacted (optionally admixed with a fluid diluent) passes through it from an entry side thereof to an exit side, said element having a conformation whereby all fluid so passing through it is subjected to substantially identical isothermal reaction conditions and being capable of providing a fluid residence time therein of at least within the range 1 to 50 milliseconds;

(b) heating means for heating the reactor element by electromagnetic induction, (c) entry conveyance means for conveying a flow of fluid to be reacted to the entry side of said element for passage therethrough;

(d) exit conveyance means for conveying exit fluid away from the element; and (e) quench means for rapidly cooling hot exit fluid from the element.

The element of such a reactor may e.g. be made of graphite, carbon or conductive metal. The element could for example be made of sintered, substantially non-fibrous conductive particles of such materials so as to provide a porous structure; this could e.g. have the configuration of a thin hollow porous cylinder so that a flow of fluid may pass radially through it either entering from the outer surface and exiting from the inner surface or entering from the inner surface and exiting from the outer surface (preferably the former). Such an element might have a porosity (defined as the volume of the pores or voids in the element divided by the total volume of the element) within the range of 35 to 60%, more preferably 40 to 55%. Suitable porous element materials include sintered or closely packed (i.e. touching), substantially non-fibrous, conductive particles of graphite, carbon or conductive metal. Another type of reactor element which might be used is a thin hollow cylinder the material of which is not porous in nature, and where the fluid permeability is provided not by micropores but by numerous drilled radial holes extending through the thickness of the cylinder (i.e. from the outer curved surface of the cylinder to the inner curved surface) so that a flow of fluid may pass radially through it. Suitable materials for such a reactor element again include graphite, carbon or conductive metal. The results in FIGS. 1 and 2 (upper curves) and in the examples were achieved using such drilled reactor elements.

In the case of the above described types of reactor element, the residence time therein at an elevated temperature T° C. within the range used in the process of the invention may be approximately determined from the residence time at NTP (normal temperature and pressure) according to the following empirical formula:

$$\text{Residence time (T° C.)} = \text{Residence time (NTP)} \times \frac{298}{(T + 273)} \times \frac{1}{1.5}$$

(the right hand term $1/1.5$ being an expansion factor to take account of the increase in the number of moles during reaction resulting from the pyrolysis causing an increase in volumetric flow rate), where the residence time at NTP is given by:

$$\frac{\text{Reactor volume (i.e. total volume of holes or pores)}}{\text{Volumetric feed flow rate (i.e. volume of feed passing per unit of time at NTP)}}$$

The above formula gives a good approximation for residence time (T° C.) in the case of 100% CDM feed. When a diluent is present in the feed the expansion factor is reduced and the ratio $1/1.5$ is better replaced by $(1+G)/1.5+G)$, where G is the molar ratio of diluent to CDM in the feed.

It will of course be appreciated that other types of fluid-phase induction-heated reactors may be of utility for achieving the required combination of reaction conditions necessary for the process of the present invention.

As far as the process of the present invention is concerned, the fluid-phase induction-heated reactor (if employed) should be operated so that the element is heated by electromagnetic induction to a temperature within the range of 750°–980° C. and the gaseous residence time in the element is within the range of 1 to 50 milliseconds (preferably 1 to 25 milliseconds). As mentioned before, this residence time is intended to include the tim taken in the element for the gas to warm up from a low entry temperature (usually at or near ambient) to a high desired temperature (within the range 750°–980° C.) imparted by the hot element and it will be appreciated that because of the high surface area per unit volume of element, the warm-up period will be extremely short and the gas temperature attained will be similar to that of the hot element.

It can be seen that, in the case of a drilled or porous element, because of the nature of the reactor element any chemical reaction therein will take place under essentially isothermal reaction conditions. Other types of element used in fluid-phase induction-reactors should of course also be of a nature which will provide essentially isothermal conditions for the reaction therein.

The heating means for heating the reactor element by electromagnetic induction may comprise a primary coil (e.g. of copper tubing) in an alternating current circuit, with the primary coil surrounding the element (constituting the secondary coil); this is particularly convenient for a cylindrically shaped element wherein the surrounding primary coil will also be cylindrical but of wider diameter. The primary coil will of course normally be separated from the element by a reactor casing(s) and/or other structure(s) of the reactor.

Conventional or obvious entry and exit conveyance means may be used to convey the flow of fluid to and from the reactor element; these normally comprise one or more suitably connected ducts of suitable configuration and position.

When operating the reactor to effect the process of the present invention, the hot exit gas is rapidly quench-cooled on leaving the element to a lower temperature usually within a period of about 50 milliseconds (the quench time is difficult to estimate accurately, but can be approximately determined in suitable cases from the free volume in the quench zone and the gas flow rate into the quench zone). Any suitable quench means may be employed. For example, the quench means may comprise a cold inert surface (e.g. the outer surface of a water-cooled body) onto which the exit fluid flow is directed before being conveyed away from the reactor by suitable exit ducting; where a hollow cylindrical drilled or porous element is used with a fluid flow direction of from the outside to the inside of the cylinder, the cold surface is conveniently provided by the surface of a cylindrical body (made of a suitable material, usually a metal, inert to the exit gas) located inside the cylindrical element and cooled by a circulating fluid, preferably water, and so defining with the element an annular quenching zone; the cold surface of such a body (or indeed that of any shaped cold surface used) may be extended by using devices such as finds (which may reduce the volume of the quench zone and hence the time to achieve full quench cooling). The quench means may alternatively, for example, comprise a flow of inert (to the exit gas) cold fluid (usually gas or vapour although a liquid, e.g. water, can be used) directed to sweep over the exit surfaces of the element so as to mix with (and hence cool) the hot gas leaving the element or to meet the hot exit fluid just beyond the element, the mixture being conveyed away through the exit conveyance means. Combinations of more than one type of quench means may also be used.

The present invention is now illustrated by reference to FIG. 3 of the accompanying drawings illustrating in schematic form one type of induction heating reactor (in fact one with a drilled cylindrical element as described above) for use in operating one embodiment of the process of the present invention.

Figure 3:
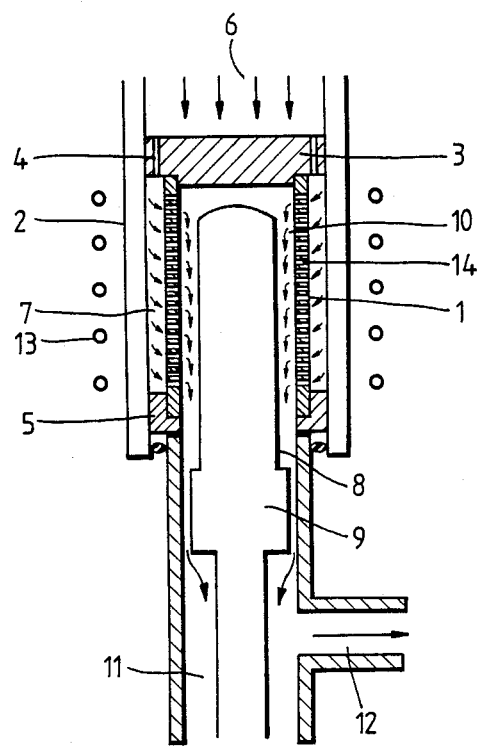

In FIG. 3, a thin, hollow and gas permeable cylindrical element 1 having numerous radial drilled holes 14 and capable of providing a gaseous residence time at operating temperatures of within the range 1 to 50 milliseconds, is located within a casing 2 of a non-conductive material (in fact in a quartz sheath) between an upper gas-tight seal 3 having an annular channel 4 near to its edge and a lower gas tight seal 5. The temperature of the element is controllably maintainable at a temperature within the range 750°–980° C. The channel 4 allows a flow of CDM for reaction (optionally admixed with a gaseous diluent) and entering the reactor through ducting 6 formed by the upper part of the casing 2, to be carried through to an annular entry zone 7 and thence radially inwards through the drilled holes of element 1 (the ducting 6, channel 4, and zone 7 comprising the last stage of fluid entry conveyance means). Exit gas from the element passes down the interior of the element and is quench-cooled by a cold-surface 8 provided by a water-cooled substantially cylindrical copper body 9 located within the element so as to define a quenching zone 10 therewith. The cold cylindrical surface may be extended if desired with devices such as fins. (It will be appreciated that the copper body could be replaced by other quench means, e.g. by a flow of cold gas, vapour of liquid spray down the inside of the cylindrical element). The cooled exit gas containing TFE, HFP, unreacted CDM, and (if used) diluent, passes out of the reactor through ducting 11 and 12 formed by the lower part of the reactor casing (comprising the first stage of the fluid exit conveyance means). The reactor gas stream may then be analysed for product composition and in a monomer production process treated by work-up means (not shown) to isolate and recover the constituents thereof.

The element 1 is rapidly heatable to a controllable temperature(s) within the range 750°–980° C. by means of an induction coil 13 in an alternating current circuit (not shown).

The present invention is further illustrated by reference to the following examples.

EXAMPLES

Reactors of the type schematically illustrated in FIG. 3 were employed for the pyrolysis of CDM. In different runs, comprising four series of experiments, namely series A, B, C and D, reaction conditions in the reaction zone were varied within the scope of the invention to achieve varying conversions for CDM. The quench time in all cases was within about 20 to 50 milliseconds. At each conversion, the selectivities for TFE and HFP formation were measured using gas chromatography.

In series A, a graphite cylindrical reactor element (radial drilled hole type) having the following characteristics was employed:
dimensions - 4.7 cm length × 19 mm outer diameter × 15 mm inner diameter
hole diameter - 0.5 mm
no. of holes - 2904
total hole volume - 1.71 ml
direction of fluid flow - radial inwards The equipment was used for the pyrolysis of 100 mole % CDM. The reaction conditions employed and the results achieved are shown in Table 1

TABLE 1

| Exp. Series | Temp (°C.) | Residence Time (milliseconds) | Conversion CDM (%) | Selectivity TFE (%) | Selectivity HFP (%) | Combined Selectivity TFE + HFP (%) |
|---|---|---|---|---|---|---|
| A. | 750 | 3.4 | 7.8 | 92.4 | 1.9 | 94.3 |
| input | 797 | 4.8 | 21.7 | 94.4 | 2.2 | 96.6 |
| feed | 800 | 3.2 | 16.1 | 92.9 | 2.9 | 95.8 |
| 100 | 850 | 3.0 | 25.0 | 88.5 | 5.6 | 94.1 |
| mole % | 850 | 4.5 | 38.2 | 85.1 | 8.4 | 93.5 |
| CDM | 852 | 9.1 | 45.8 | 82.3 | 9.9 | 92.2 |
| | 882 | 4.4 | 42.5 | 83.3 | 9.3 | 92.6 |
| | 889 | 2.9 | 31.5 | 83.8 | 11.0 | 94.8 |
| | 904 | 4.3 | 43.0 | 77.7 | 14.2 | 91.9 |
| | 904 | 8.7 | 55.9 | 70.4 | 19.7 | 90.1 |
| | 935 | 2.8 | 37.6 | 76.0 | 15.7 | 91.7 |
| | 935 | 4.2 | 50.2 | 70.0 | 19.3 | 89.3 |
| | 937 | 8.4 | 61.2 | 60.2 | 25.6 | 85.8 |

In series B, C and D, the equipment was adapted to provide a radial outward flow through a graphite cylindrical reactor element (radial drilled hole type) having the following characteristics:
dimensions - 4.7 cm length × 19 mm outer dimeter × 15 mm inner diameter
hole diameter - 1.0 mm
no. of holes - 726
total hole volume - 1.71 ml
direction of flow - radial outwards In these series, the pyrolysis was performed on a feed of CDM and nitrogen diluent, the level of CDM in series B being 50 mole %, in series C being 20 mole %, and in series D being 10 mole %. The reaction conditions employed and the results achieved are shown in Table 2.

was also used for the pyrolysis of 100 mole % CDM. In different runs, the reaction temperature inside the tube was varied within the range 750° to 900° C. to achieve varying conversions for CDM as shown in the graph of FIG. 1 (lower curve). The residence time in all cases was about 1 second. At each conversion, the combined selectivity for TFE plus HFP formation was measured (also using gas chromatography), the values obtained being shown graphically in FIG. 1 (lower curve). Carbon mass balances were also obtained for several CDM conversions, the results being shown graphically in FIG. 2 (lower curve).

It will be noted from FIG. 1 and Tables 1 and 2 that the combined selectivity of TFE plus HFP production in the new process as exemplified was ≧85% irrespective of CDM conversion (with less than 15% of other products being formed), and well over 90% for a considerable range of conversion. Even higher combined selectivities were obtained when a diluent was em-

TABLE 2

| Exp. Series | Temp (°C.) | Residence Time (milliseconds) | Conversion CDM (%) | Selectivity TFE (%) | Selectivity HFP (%) | Combined Selectivity TFE + HFP (%) |
|---|---|---|---|---|---|---|
| B. | 767 | 5.9 | 31.2 | 96.1 | 1.0 | 97.1 |
| input | 771 | 3.9 | 20.5 | 96.3 | 0.8 | 97.1 |
| feed CDM | 791 | 2.9 | 23.1 | 95.2 | 1.1 | 96.3 |
| (50 mole | 798 | 2.9 | 28.2 | 94.6 | 1.4 | 96.0 |
| %) and N$_2$ | 800 | 5.8 | 38.3 | 94.0 | 2.0 | 96.0 |
| | 800 | 3.9 | 27.7 | 96.0 | 1.7 | 97.7 |
| | 800 | 2.9 | 25.5 | 95.0 | 1.3 | 96.3 |
| | 842 | 5.5 | 60.9 | 90.5 | 3.5 | 94.0 |
| | 858 | 3.7 | 53.2 | 91.9 | 3.0 | 94.9 |
| | 855 | 2.7 | 44.7 | 92.0 | 2.8 | 94.8 |
| | 892 | 5.2 | 71.7 | 81.0 | 8.8 | 89.8 |
| | 897 | 3.5 | 65.4 | 73.0 | 19.5 | 92.5 |
| | 902 | 2.6 | 59.4 | 77.5 | 17.1 | 94.6 |
| C. | 806 | 3.2 | 29.5 | 97.6 | 1.0 | 98.6 |
| input | 796 | 4.3 | 33.0 | 96.9 | 1.0 | 97.9 |
| feed CDM | 853 | 3.1 | 47.1 | 94.6 | 2.1 | 96.7 |
| (20 mole | 850 | 4.1 | 57.0 | 93.3 | 2.6 | 95.9 |
| %) and N$_2$ | 901 | 3.0 | 66.5 | 91.3 | 4.3 | 95.6 |
| D. | 793 | 3.4 | 28.3 | 97.0 | 1.3 | 98.3 |
| input | 857 | 3.2 | 56.3 | 94.2 | 2.5 | 96.7 |
| feed CDM (10 mole %) and N$_2$ | | | | | | |

The values for the combined selectivity for TFE and HFP production at conversions of CDM over 30% for series A, B, and C are also shown graphically in FIG. 1 (top curves). Carbon balances were also determined at several CDM conversions (pyrolysis of 100 mole % CDM), the results being given graphically in FIG. 2 (top curve).

A hot tube made of "Inconel" metal (dimensions 40 cms × 1.6 cm outside of diameter × 1.0 inside diameter)

ployed. By comparison, the combined selectivity of TFE plus HFP when using the hot metal tube was always less than in the new process (as exemplified) by at least about 10%. The extremely advantageous combined TFE plus HFP selectivity as a function of HFP selectivity in the new process is also apparent. From FIG. 2, it will be noted that essentially quantitative carbon balances were obtained in the new process as exemplified, while in the exemplified hot tube process as much as 20% of the CDM fed to the tube was converted to carbon.

We claim:

1. Process for the production of tetrafluoroethylene and hexafluoropropylene which process comprises passing a gaseous flow of chlorodifluoromethane through a hot reaction zone wherein it is subjected to a pyrolysis reaction to form tetrafluoroethylene and hexafluoropropylene, followed by quench cooling of the exit flow of gas from the reaction zone, and wherein said process is subject to the following combination of conditions:

(1) the pyrolysis in the reaction zone is effected under isothermal conditions which are applied substantially uniformly to all parts of the gas passing through the zone;

(2) the isothermal temperature in the reaction zone is controllable and within the range of from 750° to 980° C.; and (3) the gaseous residence time in the reaction zone is within the range of from 1 to 50 milliseconds;

and wherein said conditions in the reactor zone are provided by using a fluid-permeable reactor element in which heat for the reaction is generated directly in the element by means of electromagnetic induction.

2. Process according to claim 1 wherein the temperature within the reaction zone is within the range 800° to 980° C.

3. Process according to claim 2 wherein the temperature within the reaction zone is within the range 840° to 980° C.

4. Process according to claim 1 wherein the temperature within the reaction zone is within the range 750° to 890° C.

5. Process according to claim 1 wherein the gaseous residence time is within the range of from 1 to 25 milliseconds.

6. Process according to claim 5 wherein the gaseous residence time is within the range of from 1 to 10 milliseconds.

7. Process according to claim 1 wherin the gaseous flow of chlorodifluoromethane includes a gaseous or vapourous diluent.

8. Process according to claim 1 wherein a part of the exit flow of gas is recycled, after having removed HCl therefrom, to the chlorodifluoromethane feed to the reactor.

9. Process according to claim 8 wherein only tetrafluoroethylene is recycled to the chlorodifluoromethane feed.

10. Process according to claim 1 wherein said process is carried out using a fluid phase electromagnetic induction-heated reactor comprising:

(a) an inductively-heatable fluid-permeable reactor element which is inductively heatable to a controllable temperature(s) of at least within the range of 750° to 980° C. to provide an isothermal reaction zone therein when fluid to be reacted passes through it from an entry side thereof to an exit side, said element having a conformation whereby all fluid so passing through it is subjected to substantially identical isothermal reaction conditions and being capable of providing a fluid residence time therein of at least within the range of from 1 to 50 milliseconds;

(b) heating means for heating the reactor element by electromagnetic induction, (c) entry conveyance means for conveying a flow of fluid to be reacted to the entry side of said element for passage therethrough;

(d) exit conveyance means for conveying exit fluid away from the element; and (e) quench means for rapidly cooling hot exit fluid from the element.

11. Process according to claim 10 wherein the element of said reactor which is used is made of graphite, carbon or conductive metal.

12. Process according to either claim 10 or claim 11 wherein the element of said reactor which is used has the configuration of a hollow cylinder which is porous or has radial drilled holes.

* * * * *